United States Patent [19]

Pietzsch

[11] Patent Number: 4,657,701

[45] Date of Patent: Apr. 14, 1987

[54] PERFUMERY COMPOSITIONS, PRODUCTS AND METHODS

[75] Inventor: Gerko C. Pietzsch, Cambridge, England

[73] Assignee: Bush Boake Allen Limited, London, England

[21] Appl. No.: 752,134

[22] Filed: Jul. 5, 1985

[30] Foreign Application Priority Data

Jul. 5, 1984 [GB] United Kingdom ................. 8417183

[51] Int. Cl.⁴ ........................... A61K 7/46; C11B 9/00
[52] U.S. Cl. .............................. 252/522 A; 252/522 R
[58] Field of Search ....................... 252/522 R, 522 A

[56] References Cited

FOREIGN PATENT DOCUMENTS 0164063 10/1982 Japan .............................. 252/522 A
168912 10/1984 Japan .............................. 252/522 A

OTHER PUBLICATIONS

Johnson Co. "Chemical Abstracts", vol. 98, 1983, p. 349 98:404254x.

*Primary Examiner*—Werren B. Lone
*Attorney, Agent, or Firm*—Kane, Dalsimer, Kane, Sullivan and Kurucz

[57] ABSTRACT

A perfume composition comprises a water immiscible film-forming solution of a perfume in a water immiscible solvent and, substantially homogeneously mixed with the solution, at least one water soluble additive, generally including a foaming agent. The composition can be discharged into a toilet bowl during flushing whereupon the water soluble additives will impart a desired effect to the water in the bowl and the perfume and the solvent will form a film on the water in the bowl after flushing, so as to perfume the room area surrounding the bowl.

12 Claims, No Drawings

PERFUMERY COMPOSITIONS, PRODUCTS AND METHODS

This invention relates to the perfuming of a room area surrounding a water-flush toilet.

In one known method of perfuming such an area a solid block (a rim block) is suspended from the rim of the toilet bowl and emanates a pleasant perfume. Perfume may be dissolved from this block into the water in the bowl during flushing.

In another method a dilute perfumed composition contains a small amount of perfume, a large amount of water or water miscible diluent, and various additives such as foaming agent and dye. The perfume is water miscible or is rendered water miscible by the presence of, for instance, an emulsifying agent. This composition is dispensed into the tank of the toilet cistern, with the result that when the toilet is flushed the water that accumulates in the bowl is perfumed. However, much of the perfumed water is flushed away and so the perfume is wasted. Although the water in the bowl contains some perfume its amount is very low and so the perfuming effect in the room containing the toilet bowl is also low. It may therefore be necessary to provide in the room an air freshener block or to freshen the air with an aerosol.

In JP No. 57164063 (CA 98:40425X) oily perfumes and surfactants are mixed to produce a composition which forms a film on water and does not disperse into water. For instance 0.5 ml of a composition of perfume and a surfactant is dripped into a flushing toilet bowl to form an oily film. It is possible to include other oil or fat in the composition, namely hydrocarbons preferably kerosene or liquid paraffin, fatty acids, high molecular weight alcohols, silicone oils or fatty acid esters. Although such compositions can give a powerful perfuming effect around a toilet and can reduce the amount of perfumed composition that is wastefully flushed away (if the oily composition is dripped into the bowl at the correct time) these compositions incur several disadvantages. Firstly, manual dispensing of the compositions into the bowl is inconvenient and any attempt at dispensing them automatically, for instance in the general method known for dispensing water-soluble perfume compositions, results in an appearance that the consumer generally finds unpleasant. This is because consumers expect perfumed flush water to have a foamy appearance during flushing and if the oily, film-forming, compositions described in JP No. 57164063 are included in the flush water these compositions inevitably prevent formation of a foam and leave an oily film on the bowl. Accordingly it is unacceptable to the consumer. Another serious disadvantage is that the oily composition tends to attack the plumbing fittings, such as gaskets and pipes, now being used in modern plumbing with the result that over a period of months leakage will occur. Accordingly the compositions described in JP No. 57164063 give an appearance that is unacceptable to the consumer and will cause serious physical damage to modern plumbing fittings.

A perfume composition according to the invention comprises a water immiscible, film-forming solution of a perfume in a water immiscible solvent and, substantially homogeneously mixed with the solution, at least one water soluble additive selected from foaming agents, colourants and anti-bacterial agents, whereby upon agitating the composition with water then at least one water soluble additive dissolves into the water and the perfume and solvent form a film on the water.

As a result of including water soluble additives it is possible to treat the water in the bowl with any of the conventional additives that are desirable, including those that the consumer believes to give a good effect, for instance a foaming agent. As a result of including water immiscible solvent it is possible to formulate the composition such that it does not physically attack modern plastics and other plumbing equipment.

It is very surprising that the damaging effects of perfume oils on plumbing equipment can be satisfactorily minimised or eliminated by dilution with an immiscible solvent that does not interfere with the other properties of the composition and it is very surprising that, despite the formation of a film of the perfume and solvent on water it is still possible to, for instance, obtain a foam of the water during flushing.

The composition must be formulated such that upon agitation with water the perfume and solvent form a film on the water and the water soluble additives dissolve into the water. It is essential that the composition is free of oil in water emulsifying agents or other materials that would emulsify the perfume and solvent into the water, since this would prevent the formation of the desired film. It is generally necessary for the composition to be substantially non-aqueous since the presence of any significant amount of water in a stable composition would necessitate the presence of an emulsifying component that would tend to emulsify the perfume solution into water during flushing.

The solution of perfume in water immiscible solvent must have positive spreading characteristics over the water in order that it does not remain, when present in small amounts, as globules on the water. The choice of the solvent may facilitate spreading of the film but generally the composition includes surfactant to serve as film promoting spreading agent. The amount of the surfactant, and the nature of the surfactant, must be such as to promote the formation of a film without causing substantial emulsification of the perfume into the water. For instance, if too much film promoting surfactant is included it may render the composition emulsifiable in water, as a result of which a film will not be formed on the water.

The surfactant must be oil soluble, in that it will remain in the film rather than disperse or dissolve into the water. Normally it has an HLB of from 8 to 11, for instance around 9.5. Preferred film promoting surfactants are non-ionic, for instance alkoxylated sorbitan esters. A particularly suitable material is ethoxylated sorbitan septaoleate, such as the material having about 40 ethoxy groups and sold at Atlas Chemical under the trade name Arlatone T. Another very suitable class of materials are fatty alcohols that have been alkoxylated with a short chain of, for instance, about 2 to about 5 alkoxy groups, generally ethoxy groups, for instance the 3 mole ethoxylate of oleyl alcohol, such as the material sold by Croda Limited under the trade name Volpo N3. The amount of film promoting surfactant is generally from 0.1 to 10% by weight of the composition, most preferably from 0.2 to 5%.

The compositions of the invention will normally contain a much higher proportion of perfume than conventional perfume compositions. In practice the composition usually contains at least 8% by weight perfume and generally at least 10%, and usually at least 15%, by weight perfume. In most compositions the preferred amount of perfume is 15 to 30% but sometimes it is advantageous for as much as 50%.

Generally, the perfume used in the compositions is a blended perfume based on one or more oils selected from, for instance, pine, lavender, orange or other citrus oils, together with optional additional ingredients to give the desired perfume effect.

The diluent must be present in an amount sufficient to dilute the effect of the perfume sufficiently to prevent attack on to plumbing fittings by the perfume film. Generally the ratio perfume:solvent is between 1:1 and 1:5 but it can be higher. The amount of solvent is generally in the range 30 to 90%, most preferably 50 to 85% by weight of the composition. The solvent must not solvate or emulsify the perfume into water. Solvents that can be used for diluting perfume oil to form a water immiscible film include phthalates and other esters but many of these may not reduce the attack by perfume on to plumbing fittings. Other solvents that can be used include, for instance, liquid paraffin but this prevents the appearance of any foam during flushing and so tends not to appeal to the consumer.

We have surprisingly found that it is possible to reduce or eliminate attack by the composition on plumbing fittings and to permit transient foam formation during flushing if we use as the water immiscible solvent aliphatic branched chain hydrocarbon containing at least 10 carbon atoms. Preferably the ratio of the number of chain carbon atoms to methyl or other alkyl groups substituted into the chain is 3:1 to 1:1, preferably 2:1 to 1:1 and most preferably 1:1. Preferably chain atoms are disubstituted. The most suitable material is the material that is commercially available under the name Isododecane.

Preferred water immiscible solvents that can be used in the invention have the formula $$(CH_3)_3C[CH_2C(CH_3)CH_2]_nC(CH_3)_3$$

where n is a small number that is generally 1 or, less preferably, 2 or even 3. These solvents can conveniently be made by oligomerisation of isobutylene followed by hydrogenation.

The water soluble additives are preferentially soluble in water such that they go into the aqueous phase rather than the oil film. However they must be compatible with the other components of the composition.

One suitable additive is an oil compatible, water soluble, blue or other dye and that will have the effect of colouring the water. A suitable amount is from 0.001 to 1% by weight of the composition.

The composition may include an antibacterial that is oil compatible but water soluble. Typical amounts are from 0.1 to 5% by weight of the composition.

The composition preferably includes a water soluble, oil compatible, foaming surfactant in order to cause foaming of the water during flushing. However, this surfactant must be of a nature, and in an amount, such that it does not prevent the formation of a film after flushing. Suitable amounts are from 0.5 to 10%, typically from 1 to 5% by weight of the composition.

Suitable materials are generally non-ionic. One class from which they may be selected include the alkyl phenol ethyoxylates such as nonyl phenol ethoxylates, preferably having HLB from 11 to 15, most preferably around 13. These compounds may have, for instance, about 5 to about 15, preferably around 9, ethoxy groups. Another class of foaming surfactants are the fatty alcohol ethoxylates such as the ethoxylates of lauryl alcohol or cetyl alcohol having 5 to 20 ethoxy groups.

The composition preferably consists substantially only of the perfume, the isododecane or other water immiscible solvent, a film promoting, oil soluble, surfactant (as the components of the water immiscible film forming solution) and the one or more water soluble additives.

The composition is preferably formulated as a liquid. It may be dispensed manually onto the water of the bowl, for instance after flushing, either from a free-standing bulk container or from a dispenser in the bowl, for instance, attached to the rim or in the downpipe leading to the bowl. Alternatively, it may be dispensed from such dispensers automatically in response to flushing of the bowl, preferably being dispensed at the end of each flush.

Preferably, the composition is discharged in the cistern in response to flushing of the bowl and in particular it is preferred to dispense it in the cistern in such a way that it forms a film on the water in the cistern. Since the water in the cistern is relatively static most or all of the water soluble ingredients may remain in the film. Upon flushing the toilet the film enters the bowl after most of the water in the cistern and so loss of perfume in flush water is minimised. Agitation of the composition with the water occurs during flushing and so foaming will occur even though the perfumed water immiscible film will tend to collect after flushing to destroy the foam.

The invention includes also a container containing the composition and provided with means for discharging a predetermined volume of the composition, generally in response to the emptying or filling of a cistern or other tank in which the container is positioned.

In use the container generally has a downwardly facing outlet controlled by a float valve that drops, and permits discharge of the predetermined volume, when the water level in the tank falls below the position of the outlet. The float valve preferably carries or includes a cup for measuring the predetermined volume, the cup and the outlet being constructed so that flow of composition from the container into the cup ceases when the cup has collected the predetermined volume.

For instance with the container initially positioned in the tank when the water level is high, the float valve closes the outlet. When the tank is emptied the float valve drops and opens the outlet to permit composition to flow into the cup. When the desired volume has collected in the cup the composition seals the discharge outlet and so prevents any further composition flowing from the container. Generally the amount held in the cup is from 0.5 to 2 cc, typically around 1 cc. When the tank refills with water the water will force the float valve up and the composition will rise out of the cup and form a film on the top of the water in the tank.

When a cistern filled with water having a surface film of highly perfumed oil is emptied from its base during flushing the main volume of water washes through the toilet bowl whilst the perfume oil remains in the cistern, and the perfume oil is washed into the toilet bowl only after the majority of the water, and so little or none of the oil is lost from the toilet.

The compositions of the invention can also be discharged manually or automatically on to any reservoir of liquid, for example a drain, where it is required to modify the properties of the liquid and to provide effective local perfuming.

The following are examples of the invention.

EXAMPLE 1

A composition comprises, in percentage by weight, 20% of a citrus perfume blend, 72.95% isododecane, 2% oleyl alcohol 3 mole ethoxylate (Volpo N3), 5% nonyl phenol 9 mole ethoxylate (Surfac NO90 from Surfachem Limited) and 0.05% acid blue 62 (Lissamine Blue 2BR from ICI Limited). The composition is packed in a bottle provided with an outlet cap that includes a measuring cup and a float valve. The bottle is placed in the cistern upside down so that, when the cistern is empty, the valve opens and fills the cap, whereupon further flow from the bottle ceases. When the cistern fills with water the cap rises and closes the valved outlet and the composition in the cap floats to the surface of the cistern to form a film. Some, but not all, of the water soluble dye and surfactant dissolves into the water, the majority remaining in the film. When the toilet is flushed the initial flush water contains some of the dye and foaming agent but none of the perfume, whilst the final flush water contains all the perfume together with foaming agent and dye. Accordingly foaming occurs during the flushing but very quickly after flushing is completed a continuous film of the perfume and isododecane forms across the water in the bowl of the toilet.

EXAMPLE 2

Similar results are obtained when the composition of Example 1 is modified by the use of 25% of a lavender perfume and 67.95% isododecane, the other materials being unchanged.

EXAMPLE 3

Similar results to Example 1 are obtained when the isododecane is replaced by isohexadecane.

I claim:

1. A perfume composition comprising a water immiscible film-forming solution of a perfume in a water immiscible solvent which is an aliphatic branched chain hydrocarbon containing at least 10 carbon atoms; and substantially homogeneously mixed with the solution, at least one water soluble additive selected from foaming agents, colourants and anti-bacterial agents, whereby upon agitating the composition with water the at least one additive dissolves into the water and the perfume and solvent form a film on the water.

2. A composition according to claim 1 in which the solvent is isododecane.

3. A composition according to claim 1 in which the solvent is a compound of the formula

$(CH_3)_3C[CH_2C(CH_3)CH_2]_nC(CH_3)_3$ where n is selected from 1, 2 and 3.

4. A composition according to claim 1 that is substantially non-aqueous and that consists essentially of 0.1 to 15% by weight of the said water soluble additives and 85 to 99.9% by weight of the said water immiscible film-forming solution and includes 8 to 50% by weight of the perfume, 30 to 90% by weight of the water immiscible solvent and 0.1 to 10% by weight of an oil soluble, film promoting, surfactant.

5. A composition according to claim 4 containing 15 to 30% by weight of the perfume, 50 to 85% by weight of the solvent and 0.2 to 5% by weight of the surfactant.

6. A composition according to claim 1 in which the weight ratio perfume:solvent is 1:1 to 1:5.

7. A composition according to claim 1 in which the water soluble additives are selected from 0.1 to 5% by weight of an anti-bacterial agent, 0.5 to 10% by weight of a water soluble foaming surfactant and 0.001 to 1% by weight of a water soluble dye.

8. A composition according to claim 1 including oil soluble non-ionic surfactant that will promote formation of a water insoluble film and a water soluble non-ionic surfactant that will promote foaming when the composition is agitated with water.

9. A composition according to claim 8 in which the oil soluble surfactant is an alkoxylated fatty alcohol having about 2 to about 5 alkoxy groups per mole and the water soluble surfactant is an alkoxylated alkyl phenol condensate having about 5 to about 15 alkoxy groups per mole.

10. A container containing a composition according to claim 1 and provided with means for discharging a predetermined volume of the composition, when the container is inverted, in response to the filling of a tank in which the container is located.

11. A method of perfuming an area surrounding a water-flush toilet having a toilet bowl comprising dispensing a composition according to claim 1 into the bowl during flushing and thereby dissolving the water soluble additives into the water in the bowl and forming a film of the perfume and the water immiscible solvent on the water in the bowl.

12. A method according to claim 11 in which the dispensing of the composition into the water in the bowl is effected by discharging the composition into a cistern that contains water that is to be flushed into the bowl so as to form a film of the composition on the water in the cistern and then emptying the cistern from its base during flushing whereby the perfume oil is washed into the bowl only after the majority of the water from the cistern.

* * * * *